United States Patent
Asiri et al.

(10) Patent No.: US 10,947,255 B2
(45) Date of Patent: Mar. 16, 2021

(54) NANOCOMPOSITE CONTAINING HOLLOW SILICA SPHERES FUNCTIONALIZED WITH AZOLE SILANES

(71) Applicant: Imam Abdulrahman Bin Faisal University, Dammam (SA)

(72) Inventors: Sarah Mousa M. Asiri, Dammam (SA); Ayhan Bozkurt, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 16/448,469

(22) Filed: Jun. 21, 2019

(65) Prior Publication Data

US 2020/0399290 A1 Dec. 24, 2020

(51) Int. Cl.
*C07F 7/10* (2006.01)

(52) U.S. Cl.
CPC ..................... *C07F 7/10* (2013.01)

(58) Field of Classification Search
CPC .................. C07F 7/0803; C07F 7/10
See application file for complete search history.

(56) References Cited

U.S. PATENT DOCUMENTS

2008/0021147 A1  1/2008  Lin

FOREIGN PATENT DOCUMENTS

| CN | 101797481 A | 8/2010 |
| CN | 103170255 A | 6/2013 |
| CN | 104927418 A | 9/2015 |
| CN | 106582535 A | 4/2017 |

OTHER PUBLICATIONS

Ossiander. Journal of Membrane Science, 2014, 454, 12-19 (Year: 2014).*
: ASIRI. Applied Biochemistry and Biotechnology, 2019, 189, 760-773, available online May 22, 2019 (Year: 2019).*
Almahdali ; Confinement in Soft Materials: System Synthesis and Applications ; Dissertation ; Oct. 2017 ; 153 Pages.
Celik, et al. ; Novel triazole functional solegel derived inorganiceorganic hybrid networks as anhydrous proton conducting membranes ; Polymer 52 ; pp. 4670-4675 ; Aug. 28, 2011 ; 6 Pages.
Saad, et al. ; Ligand-modified mesoporous silica SBA-15/silver hybrids for the catalyzed reduction of methylene blue ; RSC Advances Issue 62 ; 2016 ; Abstract Only ; 2 Pages.
Jung, et al. ; Multifunctional Hybrid Silica Particles for Multicolor Imaging and Multiplex Tasking ; Nature Precedings ; Feb. 22, 2008 ; 12 Pages.

* cited by examiner

*Primary Examiner* — Noble E Jarrell
(74) *Attorney, Agent, or Firm* — Oblon, McClelland, Maier & Neustadt, L.L.P.

(57) ABSTRACT

A nanocomposite containing azole modified hollow silica spheres. In particular, the nanocomposite involves a silanization reaction product of an azole-functionalized silane linker and hollow silica spheres. The azole-functionalized silane linker is produced via a ring-opening reaction a silane coupling agent having an epoxide group and an azole compound. A method of making the nanocomposite is also specified.

18 Claims, 13 Drawing Sheets

NANOCOMPOSITE CONTAINING HOLLOW SILICA SPHERES FUNCTIONALIZED WITH AZOLE SILANES

BACKGROUND OF THE INVENTION

Technical Field

The present disclosure relates to a nanocomposite produced from silanization reactions of hollow silica spheres and an azole-functionalized silane linker, and methods of making the hollow silica spheres, the azole-functionalized silane linker, and the nanocomposite.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Recently, hollow silica spheres (HSS) with high hardness and porosity have become a promising nonmetallic material for medical, biomedical, and various industrial applications. Hollow silica spheres having dimensions in the nanometer to micrometer ranges may be utilized as therapeutic agents in drug delivery and biomolecular release systems, as well as imaging agents for medical diagnostics.

Despite these benefits, there is still a need to develop more efficient functionalization methodologies to prepare customized hollow silica spheres suitable for specific medical applications, particularly in cancer treatment and tumor therapy.

In view of the forgoing, one objective of the present disclosure is to provide a nanocomposite involving a silanization reaction product of hollow silica spheres and azole-functionalized silane linkers. Another objective of the present disclosure is to provide a method for producing the nanocomposite via post-functionalization of hollow silica spheres.

BRIEF SUMMARY OF THE INVENTION

According to a first aspect, the present disclosure relates to a nanocomposite comprising a silanization reaction product of a hollow silica sphere including a silica-containing shell surrounding a core, and an azole-functionalized silane linker, wherein (i) the silica-containing shell has a higher density of silica compared to the core, (ii) the hollow silica sphere has an average diameter of 300-900 nm, (iii) the azole-functionalized silane linker is a ring-opening reaction product of a coupling agent of formula (I)

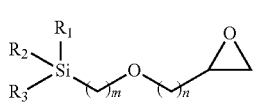

and an azole moiety, wherein $R_1$ and $R_2$ are independently an optionally substituted $C_1$-$C_6$ alkoxy, $R_3$ is selected from the group consisting of an optionally substituted $C_1$-$C_6$ alkoxy, an optionally substituted alkyl, and an optionally substituted cycloalkyl, m is an integer in a range of 2-10, and n is an integer in a range of 1-6, and (iv) a weight ratio of the hollow silica sphere to the azole-functionalized silane linker is in a range of 2:1 to 50:1.

In one embodiment, $R_1$ and $R_2$ are independently a methoxy, or an ethoxy.

In one embodiment, $R_3$ is selected from the group consisting of a methoxy, an ethoxy, a methyl, and an ethyl.

In one embodiment, m is 3.

In one embodiment, n is 1.

In one embodiment, the coupling agent of formula (I) is (3-glycidyloxypropyl)-trimethoxysilane, (3-glycidyloxypropyl)-triethoxysilane, or both.

In one embodiment, the azole moiety is at least one selected from the group consisting of 1H-1,2,4-triazole, 3-amino-1,2,4-triazole, and 5-aminotetrazole.

In one embodiment, a molar ratio of the coupling agent of formula (I) to the azole moiety is in a range of 1:2 to 2:1.

In one embodiment, the hollow silica sphere comprises at least 85 wt % of silica relative to a total weight of the hollow silica sphere.

In one embodiment, the silica-containing shell has a thickness in a range of 100-250 nm.

In one embodiment, the core has a diameter of 100-400 nm.

According to a second aspect, the present disclosure relates to a method of preparing the nanocomposite of the first aspect. The method involves the steps of (i) mixing a hydrolyzable aryl silane and an acid in an aqueous solution to form a hydrolyzed silane solution, (ii) mixing the hydrolyzed silane solution with a hydroxide base to form a precipitate, (iii) drying the precipitate to form a hollow silica sphere, (iv) reacting a coupling agent of formula (I)

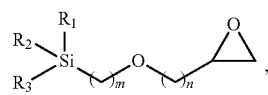

with an azole moiety to form an azole-functionalized silane linker, (v) mixing the hollow silica sphere and the azole-functionalized silane linker to form a mixture, and (vi) heating the mixture, thereby forming the nanocomposite, wherein: $R_1$ and $R_2$ are independently an optionally substituted $C_1$-$C_6$ alkoxy, $R_3$ is selected from the group consisting of an optionally substituted $C_1$-$C_6$ alkoxy, an optionally substituted alkyl, and an optionally substituted cycloalkyl, m is an integer in a range of 2-10, n is an integer in a range of 1-6, and a weight ratio of the hollow silica sphere to the azole-functionalized silane linker is in a range of 2:1 to 50:1.

In one embodiment, the precipitate is dried at a temperature in a range of 50-150° C. In one embodiment, the reacting occurs in an alcohol at a temperature in a range of 50-150° C.

In one embodiment, the mixture has a pH of 9-11.

In one embodiment, the heating is conducted at a temperature in a range of 40-100° C. In one embodiment, the hydrolyzable aryl silane is trimethoxyphenylsilane.

In one embodiment, the acid is nitric acid, and the hydroxide base is ammonium hydroxide.

In one embodiment, the coupling agent of formula (I) is (3-glycidyloxypropyl)trimethoxysilane, (3-glycidyloxypropyl)triethoxysilane, or both.

In one embodiment, the azole moiety is at least one selected from the group consisting of 1H-1,2,4-triazole, 3-amino-1,2,4-triazole, and 5-aminotetrazole.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
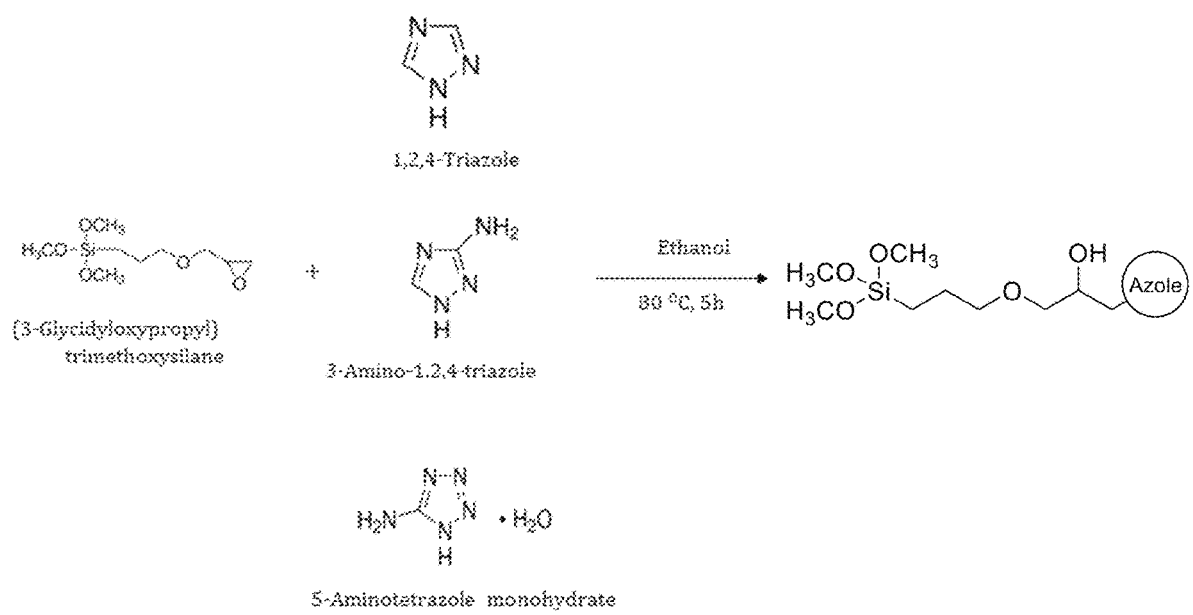
FIG. 1 is an illustration showing a synthesis scheme of azole-functionalized coupling agents.

Embodiments of the present disclosure will now be described more fully hereinafter with reference to the accompanying drawings, in which some, but not all embodiments of the disclosure are shown.

The present disclosure will be better understood with reference to the following definitions. Unless otherwise specified, "a" or "an" means "one or more". Within the description of this disclosure, where a numerical limit or range is stated, the endpoints are included unless stated otherwise. Also, all values and subranges within a numerical limit or range are specifically included as if explicitly written out.

As used herein, the terms "compound", "product", and "coupling agent" are used interchangeably, and are intended to refer to a chemical entity, whether in the solid, liquid or gaseous phase, and whether in a crude mixture or purified and isolated.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyridyl, pyrimidiyl, and the like), substituted heterocyclyl and mixtures thereof and the like. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

As used herein, the term "alkyl" unless otherwise specified refers to both branched and straight chain saturated aliphatic primary, secondary, and/or tertiary hydrocarbons of typically C$_1$ to C$_{21}$, for example C$_1$, C$_2$, C$_3$, C$_4$, C$_5$, C$_6$, C$_7$, C$_8$, C$_9$, C$_{10}$, C$_{ii}$, C$_{12}$, C$_{13}$, C$_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "aryl", as used herein, and unless otherwise specified, refers to phenyl, biphenyl, naphthyl, anthracenyl, and the like. The term "aryl" also includes a "heteroaryl" which is an aryl group where at least one carbon atom is replaced with a heteroatom (e.g. nitrogen, oxygen, sulfur) and can be indolyl, furanyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

According to a first aspect, the present disclosure relates to a nanocomposite, comprising, in reacted form, a hollow silica sphere including a silica-containing shell surrounding a core, and an azole-functionalized silane linker.

When referencing hollow silica spheres, "hollow" refers to a central area (i.e., a core portion) of a particle which has a lower density of silica compared to the surrounding structure (i.e., the shell portion). While the definition of "hollow" may encompass a continuous void that is completely free of silica, this is not a requirement, and some silica may be disposed within the core portion. By way of example, a silica particle which has a substantially continuous density of silica from one point on the particle though the center of the particle to a point directly across from it would be considered solid herein and not hollow, whereas a silica particle that has 60-80 wt % of a total silica content located in the shell portion, with the remaining 20-40 wt % of a total silica content located in the central area would be considered hollow herein. In at least one embodiment, the silica spheres used herein are not solid silica particles.

A "degree of hollowness" of the hollow silica spheres as used herein is an indicator of the density differential between the silica-containing shell and the core, with higher degrees of hollowness being associated with an increased capacity for storage (e.g., of pharmaceutical or cosmetic payloads), adsorption, etc. The degree of hollowness is defined as a maximum peak intensity of the core divided by a minimum peak intensity of the silica-containing shell, each of which are measured by transmission electron microscopy (TEM). That is, given the higher density of silica in the silica-containing shell than in the core, it is more difficult for a beam of electrons to pass through the silica-containing shell, resulting in intensity profiles that can be used to quantify this silica density disparity. The degrees of hollowness can then be calculated for the individual hollow silica spheres and averaged. In some embodiments, the hollow silica spheres used herein have an average degree of hollowness of 3, 4, 5, 6, 7 to 8, preferably 3.2 to 7.5, preferably 3.4 to 7.0, preferably 3.6 to 6.5, preferably 3.8 to 6.0, preferably 4.0 to 5.5. Such a degree in hollowness of the hollow silica spheres used herein is much higher (i.e. more hollow) than solid silica particles, which have an average degree of hollowness of about 1.

In a preferred embodiment, the hollow silica spheres used herein are spherical or substantially spherical. Sphericity is a measure of how closely the shape approaches that of a mathematically perfect sphere, and is defined as the ratio of the surface area of a perfect sphere having the same volume as a hollow silica sphere to the surface area of the hollow silica sphere (with unity being a perfect sphere). Preferably the hollow silica spheres have a high sphericity, with an average sphericity of at least 0.9, preferably at least 0.92, preferably at least 0.94, preferably at least 0.96, preferably at least 0.98, preferably at least 0.99. In some embodiments, the hollow silica spheres are classified based on roundness, and are categorized herein as being sub-rounded, rounded, or well-rounded, preferably well-rounded, using visual inspection similar to characterization used in the Shepard and Young comparison chart.

It is also envisaged that hollow silica particles in shapes other than spheres having high sphericities and roundness as described above may be used in addition to or in lieu of the hollow silica spheres. Exemplary shapes of hollow silica particles include rods, cylinders, rectangles, triangles, pentagons, hexagons, prisms, disks, platelets, cubes, cuboids, flakes, stars, flowers, and urchins (e.g. a globular particle possessing a spiky uneven surface).

In preferred embodiments, the hollow silica spheres used herein are uniform. As used herein, the term "uniform" refers to no more than 10%, preferably no more than 5%, preferably no more than 4%, preferably no more than 3%, preferably no more than 2%, preferably no more than 1% of the distribution of the hollow silica spheres having a different shape. For example, the hollow silica spheres are highly spherical (e.g., have an average sphericity of at least 0.9) and have no more than 1% of hollow silica particles in an oblong shape.

In some embodiments, the silica-containing shell has a thickness in a range of 100 to 250 nm, preferably 125 to 230 nm, preferably 150 to 210 nm, preferably 180 to 190 nm. In some embodiments, the core has a diameter in a range of 100 to 400 nm, preferably 120 to 350 nm, preferably 140 to 300 nm, preferably 160 to 250 nm, preferably 180 to 200 nm. In preferred embodiments, the silica-containing shell is of "uniform thickness", meaning an average shell thickness that differs by no more than 10%, no more than 8%, no more than 6%, no more than 4%, preferably no more than 2%, preferably no more than 1% at any given location on the silica-containing shell.

In some embodiments, the hollow silica spheres used herein have an average diameter in a range of 300 to 900 nm, preferably 350 to 850 nm, preferably 400 to 800 nm, preferably 450 to 750 nm, preferably 500 to 700 nm, preferably 550 to 650 nm, with the diameter being the longest linear distance measured from one point on the particle though the center of the particle to a point directly across from it.

"Dispersity" is a measure of the homogeneity/heterogeneity of sizes of particles in a mixture. The coefficient of variation (CV), also known as relative standard deviation (RSD) is a standardized measure of dispersion of a probability distribution. It is expressed as a percentage and may be defined as the ratio of the standard deviation (a) to the mean (g, or its absolute value |μ|), and it may be used to show the extent of variability in relation to the mean of a population. In a preferred embodiment, the hollow silica spheres of the present disclosure have a narrow size dispersion, i.e., are monodisperse, with a coefficient of variation of less than 30%, preferably less than 25%, preferably less than 20%, preferably less than 15%, preferably less than 12%, preferably less than 10%, preferably less than 8%, preferably less than 5%, preferably less than 3%, with the coefficient of variation being defined in this context as the ratio of the standard deviation to the mean diameter of the hollow silica spheres.

The hollow silica spheres may be agglomerated or non-agglomerated (i.e., the particles are well separated from one another and do not form clusters). In some embodiments, the hollow silica spheres may cluster and form agglomerates having an average diameter in a range of 2-500 µm, 10-200 µm, or 50-100 µm.

In one or more embodiments, the hollow silica sphere comprises at least 80 wt % of silica relative to a total weight of the hollow silica sphere, preferably at least 85 wt %, preferably at least 90 wt %, preferably at least 92 wt %, preferably at least 94 wt %, preferably at least 95 wt %, preferably at least 96 wt %, preferably at least 97 wt %, preferably at least 98 wt %, preferably at least 99 wt %, preferably at least 99.5 wt %, preferably at least 99.9 wt % of silica relative to a total weight of the hollow silica sphere.

The azole-functionalized silane linker is a ring-opening reaction product of a coupling agent of formula (I)

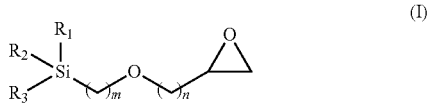

(I)

and an azole moiety.

$R_1$ and $R_2$ are each independently an optionally substituted alkoxy, preferably an optionally substituted $C_1$-$C_6$ alkoxy, preferably an optionally substituted $C_2$-$C_5$ alkoxy, preferably an optionally substituted $C_3$-$C_4$ alkoxy. In one or more embodiments, $R_1$ and $R_2$ are independently a methoxy, an ethoxy, a propoxy, an iso-propoxy, or a t-butoxy. In a preferred embodiment, $R_1$ and $R_2$ are independently a methoxy, or an ethoxy. Most preferably, $R_1$ and $R_2$ are a methoxy. $R_1$ and $R_2$ may be the same or different, preferably the same.

In one embodiment, the coupling agent is a trialkoxysilane, and $R_3$ is an optionally substituted alkoxy, preferably an optionally substituted $C_1$-$C_6$ alkoxy, preferably an optionally substituted $C_2$-$C_5$ alkoxy, preferably an optionally substituted $C_3$-$C_4$ alkoxy. In one or more embodiments, $R_3$ is a methoxy, an ethoxy, a propoxy, an iso-propoxy, or a t-butoxy. In a preferred embodiment, $R_3$ is a methoxy, or an ethoxy. Most preferably, $R_3$ is a methoxy. $R_1$, $R_2$, and $R_3$ may be the same or different, preferably the same.

In certain embodiments, one or more alkoxy groups of $R_1$, $R_2$, and $R_3$ may be replaced by other hydrolyzable functionalities such as halo (e.g. chloro, bromo, iodo, fluoro) groups.

In another embodiment, the coupling agent is a dialkoxysilane, and $R_3$ is an optionally substituted alkyl or optionally substituted cycloalkyl, preferably an optionally substituted $C_1$-$C_6$ alkyl, preferably an optionally substituted $C_2$-$C_5$ alkyl, preferably an optionally substituted $C_3$-$C_4$ alkyl. In one or more embodiments, $R_3$ is a methyl, or an ethyl.

As used herein, the value of m denotes an alkyl chain of —$CH_2$— groups connected between the silicon atom and oxygen atom on the linear alkyl chain of the coupling agent of formula (I). In one or more embodiments, m is an integer in a range of 2-10, 3-8, 4-7, or 5-6. Preferably, m is 2, 3, or 4. Most preferably, m is 3.

As used herein, the value of n denotes an alkyl chain of —$CH_2$— groups connected between the epoxide ring and oxygen atom on the linear alkyl chain of the coupling agent of formula (I). In one or more embodiments, n is an integer in a range of 1-6, 2-5, or 3-4. Most preferably, n is 1.

Exemplary coupling agents of formula (I) include, but are not limited to, (3-glycidyloxypropyl)trimethoxysilane, (3-glycidyloxypropyl)triethoxysilane, 3-glycidyloxypropylmethyl dimethoxysilane, 3-glycidyloxypropylmethyl diethoxysilane, 3-glycidyloxypropyldimethyl methoxysilane, 3-glycidyloxypropyldimethyl ethoxysilane, 2-glycidyloxyethyltrimethoxysilane, 2-glycidyloxyethyl triethoxysilane, 2-glycidyloxyethylmethyl dimethoxysilane, 2-glycidyloxyethylmethyl diethoxysilane, 4-glycidyloxybutyl trimethoxysilane, 4-glycidyloxybutyl triethoxysilane, 4-glycidyloxybutylmethyl dimethoxysilane, and 4-glycidyloxybutylmethyl diethoxysilane. Other silane coupling agents that may be used in addition to or in lieu of the coupling agent of formula (I) include, but are not limited to, 4-glycidyloxybutyldimethyl methoxysilane, 4-glycidyloxybutyldimethyl ethoxysilane, 2-(3,4-epoxycyclohexyl)ethyl trimethoxysilane, 2-(3,4-epoxycyclohexyl)ethyl triethoxysilane, 3-(3,4-epoxycyclohexyl)propyl trimethoxysilane, 3-(3,4-epoxycyclohexyl)propyl triethoxysilane, [(3-ethyl-3-oxetanyl)methoxy]propyl trimethoxysilane, [(3-ethyl-3-oxetanyl)methoxy]propyl triethoxysilane, [(3-ethyl-3-oxetanyl)-methoxy]-propylmethyldimethoxysilane, and [(3-ethyl-3-oxetanyl)-methoxy]-propyl-dimethyl-dimethoxysilane.

In a preferred embodiment, the coupling agent of formula (I) is (3-glycidyloxypropyl)trimethoxysilane, (3-glycidyloxypropyl)triethoxysilane, or both. Most preferably, the coupling agent of formula (I) is (3-glycidyloxypropyl)trimethoxysilane.

Due to a considerable ring strain, epoxides are electrophiles that can undergo ring-opening reactions (ROR) upon attacks by nucleophiles such as alkoxides, thiols, Grignard reagents, and nitrogen nucleophiles e.g. amines, azides, and azoles. The azole-functionalized silane linker described herein is a ring-opening reaction product of the coupling agent with an epoxide groups and an azole moiety.

The azole moieties applicable to the present disclosure include those have at least one unsubstituted nitrogen (either as a substituent or part of a ring system) that is capable of functioning as a nucleophile and react with an epoxide in a ring-opening reaction. Exemplary azole compounds useful for the current disclosure include, but are not limited to, imidazole, pyrazole, 1H-1,2,3-triazole, 1H-1,2,4-triazole, tetrazole, pentazole. In a preferred embodiment, the azole moiety is at least one selected from the group consisting of 1H-1,2,4-triazole, 3-amino-1,2,4-triazole, and 5-aminotetrazole. In certain embodiments, amino-substituted variants of other azoles including, but not limited to, oxazole, isoxazole, 1,2,4-oxadiazole, 1,2,5-oxadiazole, 1,3,4-oxadiazole, thiazole, isothiazole, thiadiazole, 1,2,4-thiadiazole, 1,2,5-thiadiazole, and 1,3,4-thiadiazole may be used in addition to or in lieu of the aforementioned azole moieties.

In some embodiments, a molar ratio of the coupling agent of formula (I) to the azole moiety is in range of 1:2 to 2:1, preferably 1:1.5 to 1.5:1, more preferably 1:1.2 to 1.2:1, or about 1:1. However, in certain embodiments, the molar ratio of the coupling agent to the azole moiety is less than 1:2 or greater than 2:1. In a related embodiment, when the molar ratio of the coupling agent of formula (I) to the azole moiety is greater than 1:1 (i.e. the coupling agent is in molar excess), the surface of the nanocomposite may have unreacted coupling agent of formula (I). In another related embodiment, when the molar ratio of the coupling agent of formula (I) to the azole moiety is less than 1:1 (i.e. the azole is in molar excess), the surface of the nanocomposite may have unreated azole moiety.

In one embodiment, the formed azole-functionalized silane linker is represented by a formula selected from the group consisting of

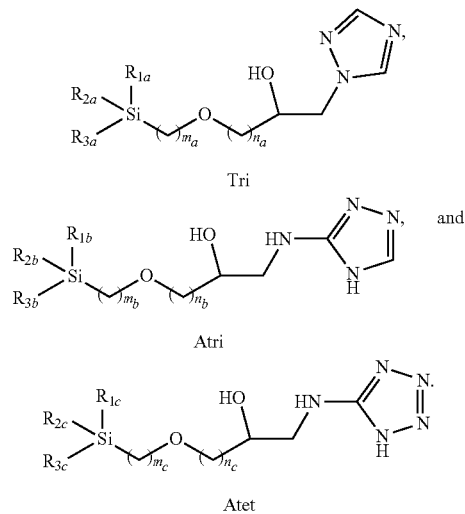

wherein $R_{1a}$, $R_{1b}$, and $R_{1c}$ are independently a $R_1$ group as previously specified, $R_{2a}$, $R_{2b}$, and $R_{2c}$ are independently a $R_2$ group as previously specified, $R_{3a}$, $R_{3b}$, and $R_{3c}$ are independently a $R_3$ as previously specified, $m_a$, $m_b$, and $m_c$ are independently an integer in a range of 2-10, 3-8, 4-7, or 5-6, preferably $m_a$, $m_b$, and $m_c$ are 3, and $n_a$, $n_b$ and $n_c$ are independently an integer in a range of 1-6, 2-5, or 3-4, preferably $n_a$, $n_b$ and $n_c$ are 1.

Silanization is a surface modification process that involves reacting hydroxy groups on a surface of a substrate (e.g. glass, silica) with a silanization agent (e.g. an alkoxysilane). The hydroxyl groups may attack and displace the hydrolyzable alkoxy groups on the silane and form a covalent Si—O—Si bond. Suitable means of silanization are generally known to those of ordinary skill in the art, and include treating a surface of the silica substrate with a silanization agent. In some embodiments, the hollow silica sphere used herein has 2-500 hydroxy groups per particle, preferably 5-200, more preferably 10-100 hydroxy groups per particle. The nanocomposite of the present disclosure is a silanization reaction product of the hollow silica sphere and the azole-functionalized silane linker. In one or more embodiments, the silicon of the silane linker forms a covalent bond to an oxygen atom of the hydroxy group on a surface of the hollow silica sphere, with the alkyloxysilane, $R_1R_2R_3$—Si—*, of the linker losing an alkoxy group, e.g., as an alcohol. Preferably, the silicon of the silane linker forms (e.g. 2 or 3) covalent bonds with oxygen atoms of hydroxy groups on multiple hollow silica spheres. Accordingly, the azole-functionalized silane linker may function as a cross-linker and connect two or more hollow silica spheres.

In some embodiments, a weight ratio of the hollow silica sphere to the azole-functionalized silane linker is in a range of 2:1 to 50:1, preferably 3:1 to 40:1, preferably 4:1 to 30:1, preferably 5:1 to 25:1, preferably 6:1 to 20:1, preferably 7:1 to 15:1, preferably 8:1 to 12:1, preferably about 10:1. However, in certain embodiments, the weight ratio of the hollow silica sphere to the azole-functionalized silane linker is less than 2:1 or greater than 50:1.

In some embodiments, the nanocomposite disclosed herein comprises an azole-functionalized silane coating that coats a surface of the hollow silica sphere. In certain embodiments, the azole-functionalized silane coating coats only a portion of a total surface of the hollow silica sphere. Specifically, the nanocomposite may have the azole-functionalized silane coating covering up to 50%, up to 60%, up to 75%, or up to 90% of a total surface of the hollow silica sphere. In a preferred embodiment, the azole-functionalized silane coating has an average thickness of 2-50 nm, 5-40 nm, 8-30 nm, 10-25 nm, or 15-20 nm. In one embodiment, the azole-functionalized silane coating is of uniform thickness. Alternatively, the azole-functionalized silane coating may be of non-uniform thickness. The term "uniform thickness" refers to an average coating thickness that differs by no more than 10%, no more than 5%, no more than 4%, no more than 3%, no more than 2%, preferably no more than 1% at any given location on the azole-functionalized silane coating of the nanocomposite. The term "non-uniform thickness" may refer to an average thickness that differs by more than 10% at any given location on the azole-functionalized silane coating.

According to a second aspect, the present disclosure relates to a method of preparing the nanocomposite of the first aspect. The method involves the steps of (i) mixing a hydrolyzable aryl silane and an acid in an aqueous solution to form a hydrolyzed silane solution, (ii) mixing the hydrolyzed silane solution with a hydroxide base to form a precipitate, (iii) drying the precipitate to form a hollow silica sphere, (iv) reacting a coupling agent of formula (I)

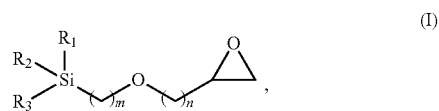

with an azole moiety to form an azole-functionalized silane linker, (v) mixing the hollow silica sphere and the azole-functionalized silane linker to form a mixture, and (vi) heating the mixture, thereby forming the nanocomposite, wherein $R_1$, $R_2$, $R_3$, m, and n are as previously specified.

The hydrolyzable aryl silane employed may be any silane having at least one aryl substituent and at least one hydrolyzable group bonded directly to the Si atom. Hydrolyzable groups include, but are not limited to, alkoxy groups (e.g., methoxy, ethoxy, propoxy, iso-propoxy, t-butoxy, as well as substituted variants, as well as mixtures of one or more of these groups) and halo groups (e.g., chloro, bromo, iodo, and fluoro), including mixtures of alkoxy and halo groups. The hydrolyzable aryl silane may therefore have one, two, or three hydrolyzable groups, preferably three hydrolyzable groups which may be the same or different, most preferably the same.

Likewise, the hydrolyzable aryl silane employed may have one, two, or three aryl groups, preferably one aryl group. In cases where the hydrolyzable aryl silane contains one aryl group, the hydrolyzable aryl silane may optionally include one or two alkyl or vinyl substituents bonded directly to the Si atom.

Exemplary hydrolyzable aryl silanes include, but are not limited to, trimethoxy(phenyl) silane, triethoxy(phenyl) silane, ethoxy(diphenyl)vinyl silane, trichloro[4-(chloromethyl)phenyl] silane, dimethoxy(diphenyl) silane, diethoxy (diphenyl) silane, diethoxy(methyl)phenyl silane, and trichloro(phenyl) silane. In preferred embodiments, the hydrolyzable aryl silane is a trialkoxy(aryl) silane, more preferably a trialkoxy(phenyl) silane, most preferably trimethoxy(phenyl) silane.

In preferred embodiments, the hydrolyzable aryl silane is the only source, reagent, or starting material used in the present disclosure to synthesize the hollow silica spheres that contains aryl functionality. In preferred embodiments, the hydrolyzable aryl silane is the only Si source utilized to prepare the hollow silica spheres in the present method, and other sources of Si, for example tetraethyl orthosilicate (TEOS), may be optionally excluded.

Hydrolysis may be carried out by dissolving the hydrolyzable aryl silane in the aqueous solution comprising, consisting essentially of, or consisting of water and an acid with optional stirring and/or heating, for example, heating to a temperature of 30-100° C., preferably 40-90° C., preferably 50-80° C., preferably 55-65° C., preferably 60° C. The amount of the hydrolyzable aryl silane dissolved in the aqueous solution may be varied, although typically a volume ratio of the hydrolyzable aryl silane to the volume of the aqueous solution ranges from 1:50 to 1:100, preferably 1:60 to 1:95, preferably 1:70 to 1:90, preferably 1:75 to 1:85. The water may be tap water, distilled water, twice distilled water, deionized water, deionized distilled water, reverse osmosis water, or various other water sources.

The acid employed in the hydrolysis reaction is preferably a mineral acid such as hydrochloric acid, nitric acid, phosphoric acid, sulfuric acid, hydrobromic acid, perchloric acid, and hydroiodic acid. In preferred embodiments, the acid is nitric acid. A concentration of the acid in the aqueous solution may vary widely, but typical concentrations range from 1-15 mM, preferably 2-13 mM, preferably 3-11 mM, preferably 4-10 mM, preferably 5-9 mM, preferably 6-8 mM.

After mixing the hydrolyzable aryl silane with the aqueous solution, the hydrolysis reaction is allowed to take place for an appropriate time to convert the hydrolyzable aryl silane into a partially or fully hydrolyzed form, whereby the hydrolyzable group (e.g., methoxy, chloro, etc.) is replaced by —OH, to form a hydrolyzed silane solution. In most cases, especially when heating is employed, less than 10 minutes, preferably less than 5 minutes, more preferably less than 3 minutes is enough to result in complete hydrolysis, although longer hydrolysis times may also be employed.

Once hydrolysis is deemed sufficiently complete, the hydrolyzed silane solution may be mixed with an appropriate hydroxide base to condense the hydrolyzed silane thereby forming a precipitate. The hydroxide base employed in the condensation reaction may be an alkali metal hydroxide (e.g., lithium hydroxide, sodium hydroxide, potassium hydroxide, rubidium hydroxide, and cesium hydroxide), an alkali earth metal hydroxide (e.g., magnesium hydroxide, calcium hydroxide, strontium hydroxide, and barium hydroxide), or an ammonium hydroxide (e.g., ammonium hydroxide, tetramethylammonium hydroxide, triethylammonium hydroxide, trimethylanilinium hydroxide, etc.). In preferred embodiments, the hydroxide base is ammonium hydroxide. The hydroxide base may be used in the form of an aqueous base solution, the concentration thereof is preferably about 10 to 50%, preferably about 20 to 40%, more preferably about 30 to 35%, most preferably about 33%, by weight of hydroxide base per total volume of the aqueous base solution.

In some embodiments, an excess of hydroxide base is combined with the hydrolyzed silane solution. For example, a molar ratio of hydroxide base employed in the condensation reaction to the acid employed in the hydrolysis reaction may be about 100:1 to 1000:1, preferably 200:1 to 900:1, preferably 300:1 to 800:1, preferably 400:1 to 700:1, preferably about 500:1. Upon addition of the hydroxide base, a precipitate generally forms immediately at ambient temperatures (i.e., 20-25° C.), or alternatively upon optional heating to 30-80° C., or 40-70° C., or 50-60° C. The resulting suspension may be allowed to settle, or alternatively may be stirred, for example with a mechanical or magnetic stirrer.

The precipitate may then be separated from the suspension, for example by filtration, centrifugation, decantation, and the like, and optionally washed with an organic solvent, water, or both. Exemplary organic solvents may include, but are not limited to $C_1$ to $C_4$ lower alkanols, for example, methanol, ethanol, isopropanol, butanol; polyols and polyol ethers, for example, glycol, 1,3-propanediol, 1,3-butanediol, 2-butoxyethanol, propylene glycol, diethylene glycol, ethylene glycol monomethyl ether, and propylene glycol monomethyl ether.

The precipitate may then be dried at a temperature of 30-150° C., preferably 50-120° C., preferably 60-100° C., or about 70° C. under standard pressure or under vacuum, thereby forming the hollow silica sphere. The method may further involve calcining the precipitate at a temperature of 180-750° C., 200-600° C., 250-500° C., or 300-400° C. to form the hollow silica sphere. In at least one embodiment, the hollow silica sphere used herein is produced without calcination.

The method of preparing the nanocomposite also involves the step of reacting a coupling agent of formula (I)

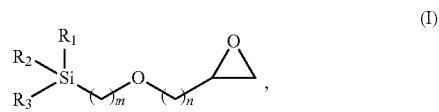

with an azole moiety to form an azole-functionalized silane linker, wherein $R_1$, $R_2$, $R_3$, m, n, and the azole moiety are as previously specified. In a preferred embodiment, the coupling agent of formula (I) is (3-glycidyloxypropyl)-trimethoxysilane, (3-glycidyloxypropyl)-triethoxysilane, or both. In another preferred embodiment, the azole moiety is at least one selected from the group consisting of 1H-1,2,4-triazole, 3-amino-1,2,4-triazole, and 5-aminotetrazole.

In a preferred embodiment, reacting the coupling agent of formula (I) having an epoxide group with the azole moiety to form the azole-functionalized silane linker is performed in a polar protic solvent, preferably an alcohol, more preferably in ethanol. Exemplary polar protic solvents that may be used in addition to, or in lieu of ethanol include, but are not limited to, methanol, n-propanol, isoproponal, n-butanol, and mixtures thereof. In some embodiments, the reaction is performed at a concentration of the azole moiety in a range of 0.01-5 M, preferably 0.1-2 M, preferably 0.15-1 M, preferably 0.2-0.5 M. In a related embodiment, molar ratio of the azole moiety to the coupling agent of formula (I) in a range of 1:2 to 2:1, preferably 1:1.5 to 1.5:1, more preferably 1:1.2 to 1.2:1, or about 1:1. In a preferred embodiment, the reaction is performed under mechanical stirring, preferably a magnetic stirrer at a temperature of up to 150° C., preferably 30-120° C., preferably 40-100° C., preferably 60-90° C., preferably 70-85° C., or about 80° C.

and has a reaction time of up to 24 hours, preferably 1-12 hours, preferably 2-10 hours, preferably 4-8 hours, or about 5 hours.

The azole-functionalized silane linker may be isolated and purified by methods known to those of ordinary skill in the art, such as crystallization, filtration through a celite containing cartridge, evaporating the reaction mixture to dryness, aqueous work-up, extraction with organic solvents, distillation, column chromatography, and high pressure liquid chromatography (HPLC) on normal phase or reversed phase. Preferred methods include column chromatography and recrystallization.

The method of preparing the nanocomposite further involves the steps of mixing the aforementioned hollow silica sphere and azole-functionalized silane linker to form a mixture, and heating the mixture thereby forming the nanocomposite. The mixture may further comprise a solvent including, but are not limited to, water, methanol, ethanol, ethylene glycol, isopropanol, propanol, n-butanol, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pet ether, pentane, hexane(s), decalin, THF, dioxane, toluene, xylene(s), o-dichlorobenzene, diethyl ether, and methyl t-butyl ether. Preferably, the solvent is water. In one embodiment, a weight ratio of the hollow silica sphere to the azole-functionalized silane linker is in a range of 2:1 to 50:1, preferably 3:1 to 40:1, preferably 4:1 to 30:1, preferably 5:1 to 25:1, preferably 6:1 to 20:1, preferably 7:1 to 15:1, preferably 8:1 to 12:1, preferably about 10:1. However, in certain embodiments, the weight ratio of the hollow silica sphere to the azole-functionalized silane linker is less than 2:1 or greater than 50:1.

For the purpose of the present disclosure, a "sol-gel material" is a material prepared via a "sol-gel" process where an oxide network formed through hydrolysis and polycondensation reactions of molecular precursor(s) in a liquid form (sol). In the present case, the molecular precursor is the azole-functionalized silane linker. As used herein, the sol-gel process is considered as "an aging process", and the "sol-gel material" obtained may be referred as a "gel". The sol (e.g. azole-functionalized silane linker) may be mixed with the aforementioned hollow silica spheres and forms a nanocomposite after aging. The aforementioned step of preparing the nanocomposite may involve a sol-gel process.

The hollow silica spheres may be mixed with the azole-functionalized silane via agitation by an agitator, a vortexer, a rotary shaker, a magnetic stirrer, a centrifugal mixer, an overhead stirrer, or a sonicator, thereby forming a mixture. Preferably, the hollow silica spheres are mixed with the azole-functionalized silane via sonication carried out in an ultrasonic bath, with an ultrasonic probe, or using an ultrasonic processor. In another embodiment, the mixture is left to stand (i.e. not agitated).

In one or more embodiments, prior to the heating, the pH of the mixture may be made basic. Preferably, the pH of the mixture is in a range of 8-11, 8.5-10.5, 9-10. Most preferably, the mixture has a pH of about 10. In a preferred embodiment, the pH of the mixture is tuned and maintained by sodium hydroxide (NaOH) but a variety of bases are envisaged, including hydroxide, carbonates, and bicarbonates of alkali metals or alkaline earth metals. The mixture may be heated (e.g. aged) at a temperature in a range of 40-120° C., preferably 50-100° C., more preferably 60-80° C., or about 70° C. for 1-48 hours, 5-36 hours, 10-30 hours, or about 24 hours, thereby forming the nanocomposite. The nanocomposite may be washed by ethanol and/or water, and then filtered and dried.

The nanocomposite may be useful in a range of applications, including medical therapy delivery/carrier, imaging, gene transfer, sensing, catalysis, filler material, construction material, and the like. In particular, the azole moieties on the hollow silica spheres allow the nanocomposite to exhibit therapeutic activities such as antimicrobial (e.g. antifungal, antibacterial, antiviral, antimycobacterial), anti-cancer, antioxidant, as well as anti-inflammatory efficacies.

The examples below are intended to further illustrate protocols for preparing and characterizing hollow silica spheres, azole-functionalized silica linker, and nanocomposite, and uses thereof, and are not intended to limit the scope of the claims.

Example 1

Materials

The chemical materials including (3-glycidyloxypropyl) trimethoxysilane ($C_9H_{20}O_5Si$) (≥98%), 1,2,4-triazole $C_2H_3N_3$ (98%), 3-amino-1,2,4-triazole ($C_2H_4N_4$)(≥95%), 5-aminotetrazole monohydrate ($CH_3N_5 \cdot H_2O$) (≥97%), sodium hydroxide (NaOH), phenyltrimethoxysilane (PTMS), nitric acid ($HNO_3$), and ammonium hydroxide ($NH_4OH$) were purchased from Sigma-Aldrich, Inc. and used as received without further purification. Deionized water was used throughout this study.

Example 2

Synthesis of Hollow Silica Spheres (HSS)

0.96 mL of PTMS was dissolved in 80 mL of 6.6 mM nitric acid ($HNO_3$), and the mixture was stirred in an isothermal water bath at 60° C. The hydrolysis developed rapidly at the adjacency of the PTMS/water interface within three minutes upon the initial introduction of acid. Then, the addition of 13.6 mL of ammonium hydroxide ($NH_4OH$) solution (33%) initiated the condensation reaction. The clear mixture solution became a milky mixture immediately. The precipitated particles were removed from the condensed solution via centrifugation, and washed with ethanol and then with water. Finally, the product was dried at 70° C.

Example 3

Synthesis of 3GPS-Azole

An equimolar of (3-glycidyloxypropyl) trimethoxysilane (3GPS) (0.5 g) was mixed with 0.14 g, 0.176 g, and 0.216 g of 1,2,4-Triazole (Tri), 3-Amino-1,2,4-triazole (Atri), and 5-Aminotetrazole monohydrate (Atet), respectively. Then, 10 mL of ethanol was added to the mixture. The mixture was stirred at 80° C. for about 5 hours (FIG. 1).

Example 4

Synthesis of HSS-3GPS-Azole Nanocomposites

Figure 2:
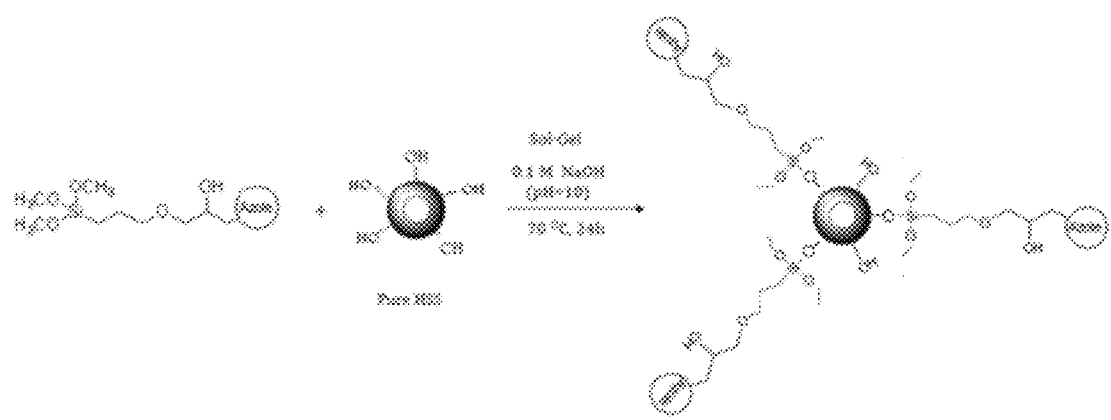
FIG. 2 is an illustration showing a synthesis scheme of a nanocomposite.

Before the sonication process, 0.5 g of pure HSS and 10 mL of water were added to each azole products (i.e. 3GPS-Tri, 3GPS-Atri, 3GPS-Atet) prepared in Example 3 to form a reaction mixture. Then 0.1 M of NaOH was added slowly to the reaction mixture to adjust the pH to 10. The reaction mixture was heated to 70° C. for 24 h. Then polymerization of HSS was performed using a simple sol-gel process. Finally, the solutions were washed until pH became natural to collect solid products, which were dried to obtain nanocomposites HSS-3GPS-Tri, HSS-3GPS-Atri, and HSS-3GPS-Atet, respectively (FIG. 2).

Example 5

Structure Characterization

The structure phase of the HSS-3GPS-Azole nanoparticles were studied by X-ray diffraction (XRD) (Shimadzu XRD-7000, with monochromatic high-intensity Cu Kα radiation ($\lambda$=1.5406 Å)) with 2θ=10-80°. FTIR analysis was conducted within the range of 400-4000 cm-using Spectrum Two from PerkinElmer. Thermogravimetric analysis (TGA) was carried out from 25° C. to 700° C. with scan rate 10° C./min under nitrogen atmosphere using STA 6000 simultaneous thermal analyzer. The morphology, features, distribution and size of the nanoparticles were confirmed by Scanning Electron Microscopy (SEM) (Inspect S50) and Transmission Electron Microscopy (TEM) (Morgagni 268). The sample for TEM analysis was prepared by dispersing the nanoparticles in ethanol to form a suspension, shaking the suspension in an ultrasonicator for 10 minutes, and then placing and drying a drop of the suspension on a carbon-coated copper grid at room temperature.

Example 6

X-Ray Diffraction Studies

Figure 3A:
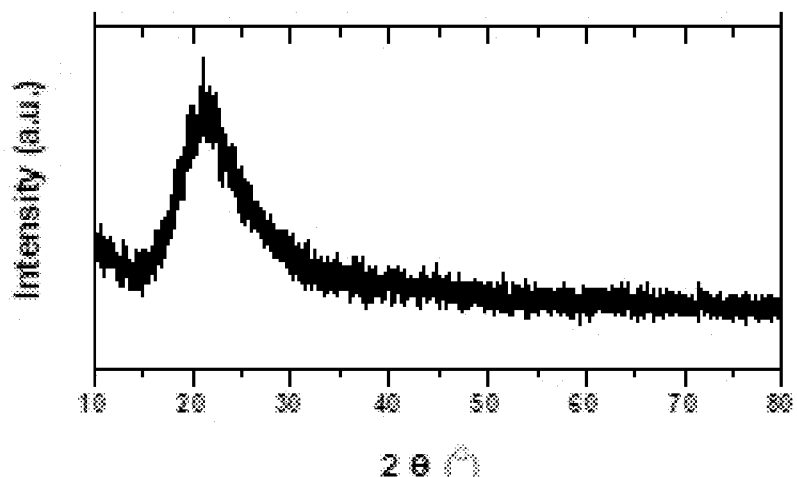
FIG. 3A shows a X-ray diffraction (XRD) pattern of a nanocomposite containing 1H-1,2,4-triazole as the azole moiety (nanocomposite HSS-3GPS-Tri).
Figure 3B:
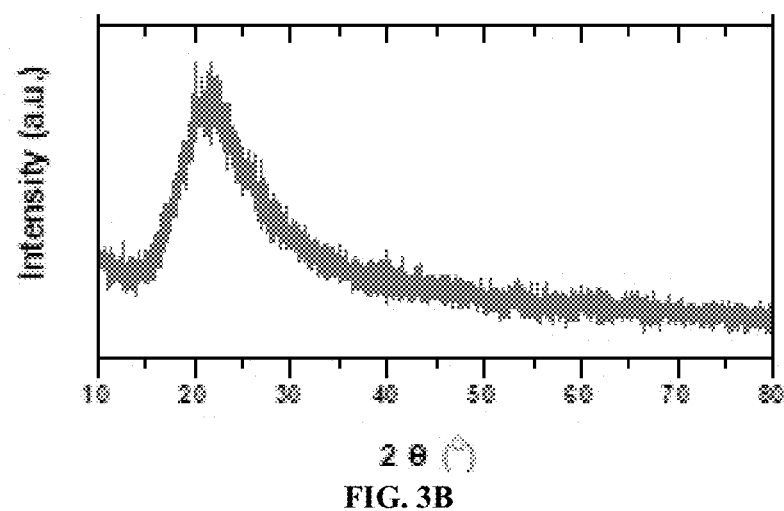
FIG. 3B shows a XRD pattern of a nanocomposite containing 3-amino-1,2,4-triazole as the azole moiety (nanocomposite HSS-3GPS-Atri).
Figure 3C:
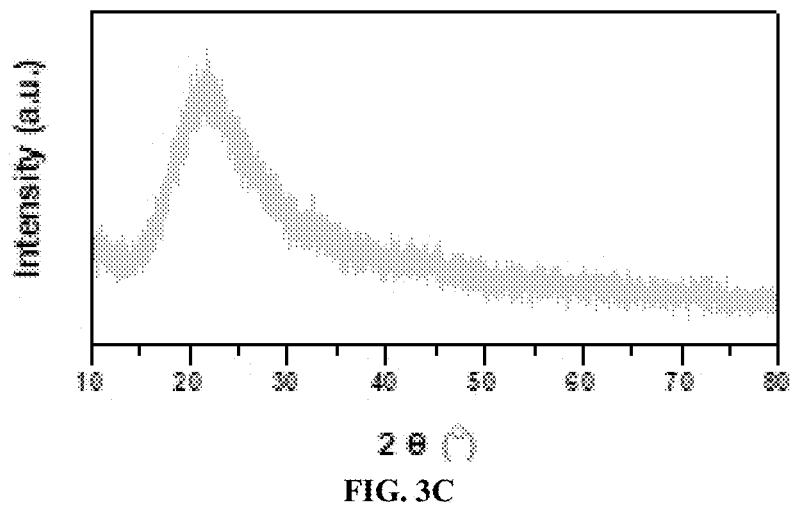
FIG. 3C shows a XRD pattern of a nanocomposite containing 5-aminotetrazole as the azole moiety (nanocomposite HSS-3GPS-Atet).

FIGS. 3A-C depict the XRD of azole group functionalized HSS nanocomposites. The spectra illustrated amorphous characteristic of HSS nanocompsites. A typical pattern for amorphous silica nanoparticles was observed without any sharp diffraction peaks. This indicated that all the samples were amorphous in nature [Qian Guo, Guoqiang Yang, Danchun Huang, Wenbin Cao, Lin Ge and Lu Li, Synthesis and characterization of spherical silica nanoparticles by modified Stöber process assisted by slow-hydrolysis catalyst, Colloid and Polymer Science (2018), Volume 296, Issue 2, pp 379-384, incorporated herein by reference in its entirety].

The samples displayed a prominent crystalline phase with reduced intensity peaks slight shifted from that of pure silica nanoparticles prepared by a previous study [Sultan Akhtar, Seyda Tugba Gunday, B. Rabindran Jermy, M. A. Almessiere, Ayhan Bozkurt, A novel approach to produce monodisperse hollow pure silica spheres, Journal of Saudi Chemical Society, Volume 23, Issue 4, pp 477-485, incorporated herein by reference in its entirety], and by a procedure reported by Nallathambi et al. (2θ=20°) [Gobi Nallathambi, Thangavelu Ramachandran, Venkatachalam Rajendran, Rajagoundar Palanivelu, Effect of Silica Nanoparticles and BTCA on Physical Properties of Cotton Fabrics, Materials Research. 2011; 14(4): 552-559, incorporated herein by reference in its entirety] to 2θ=20.98°, 20.66°, and 21.45°, while d-spacing was d=4.23 Å, 4.29 Å, and 4.14 Å for HSS-3GPS-Tri, HSS-3GPS-Atri, and HSS-3GPS-Atet, respectively. The weak intensity and increased broadness of the peaks showed that the rearrangement of particle size to nanosized amorphous form. These results indicated that there was a reaction between azole-bound (3-glycidyloxypropyl) trimethoxysilane and the hollow silica nanoparticles (HSS), which formed effective linkages for crosslinking and aggregation.

Example 7

FTIR Spectra

Figure 4A:
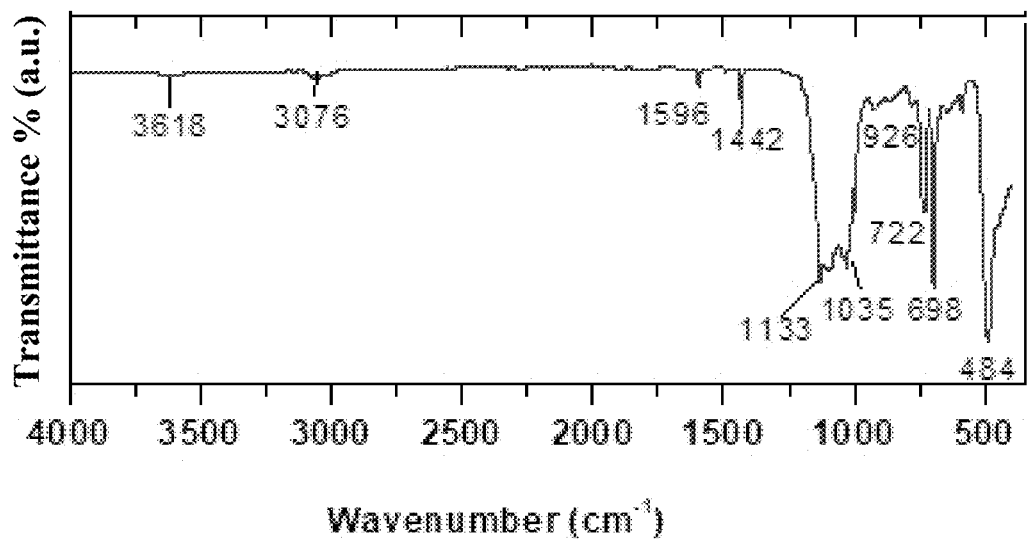
FIG. 4A is a FTIR spectrum of unmodified hollow silica spheres.
Figure 4B:
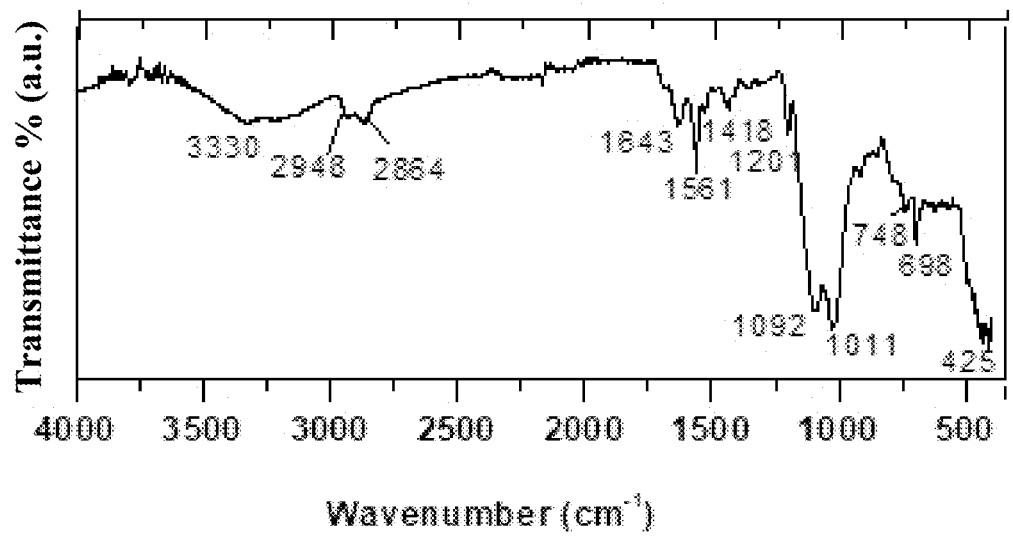
FIG. 4B is a FTIR spectrum of nanocomposite HSS-3GPS-Tri.
Figure 4C:
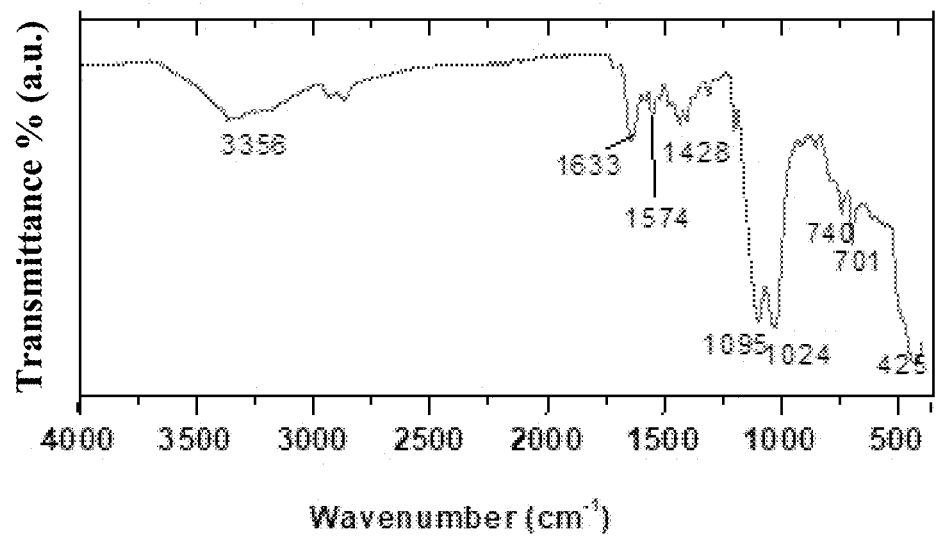
FIG. 4C is a FTIR spectrum of nanocomposite HSS-3GPS-Atri.
Figure 4D:
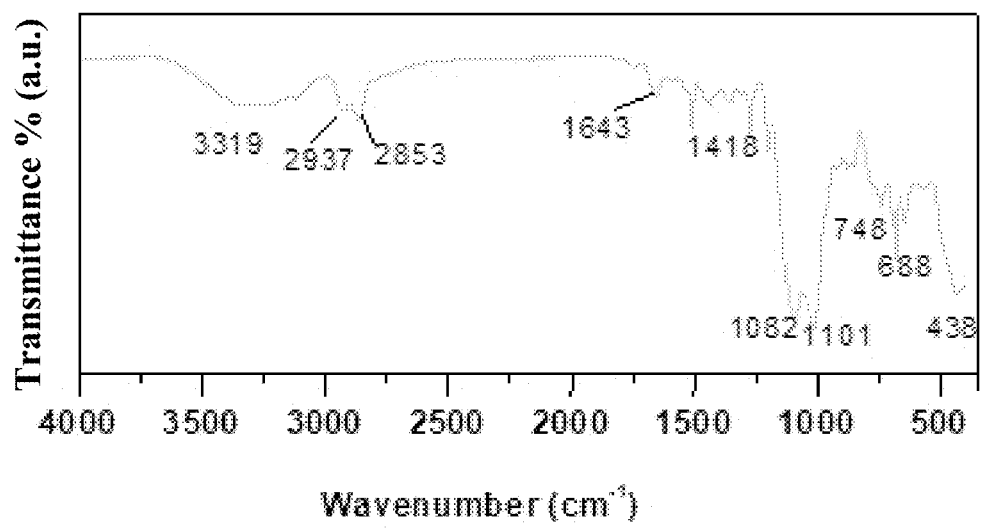
FIG. 4D is a FTIR spectrum of nanocomposite HSS-3GPS-Atet.
Figure 5A:
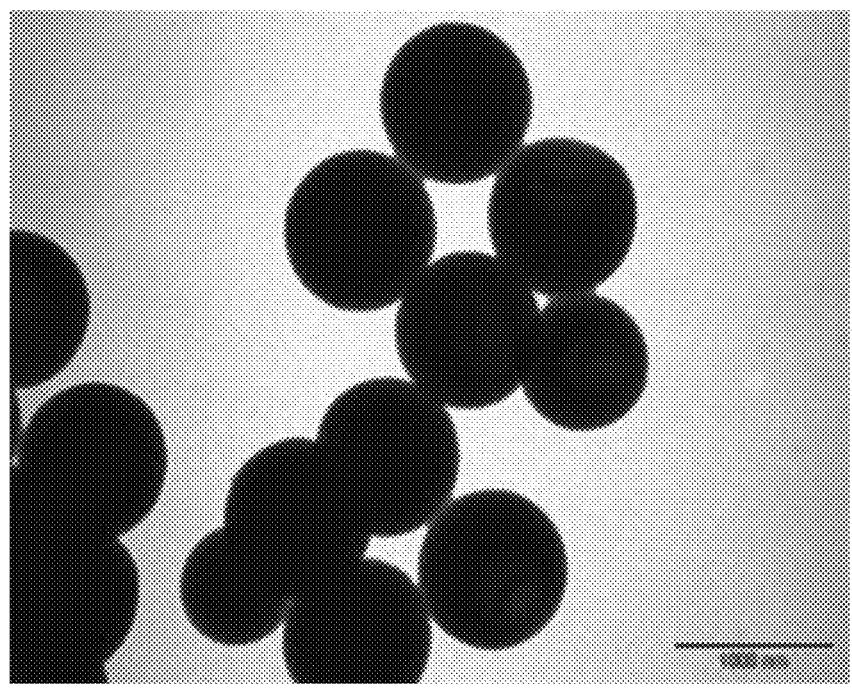
FIG. 5A is a TEM image of unmodified hollow silica spheres.
Figure 5B:
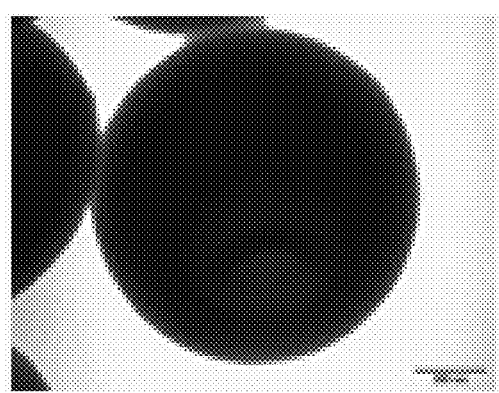
FIG. 5B shows a magnified view of the sample in FIG. 5A.
Figure 5C:
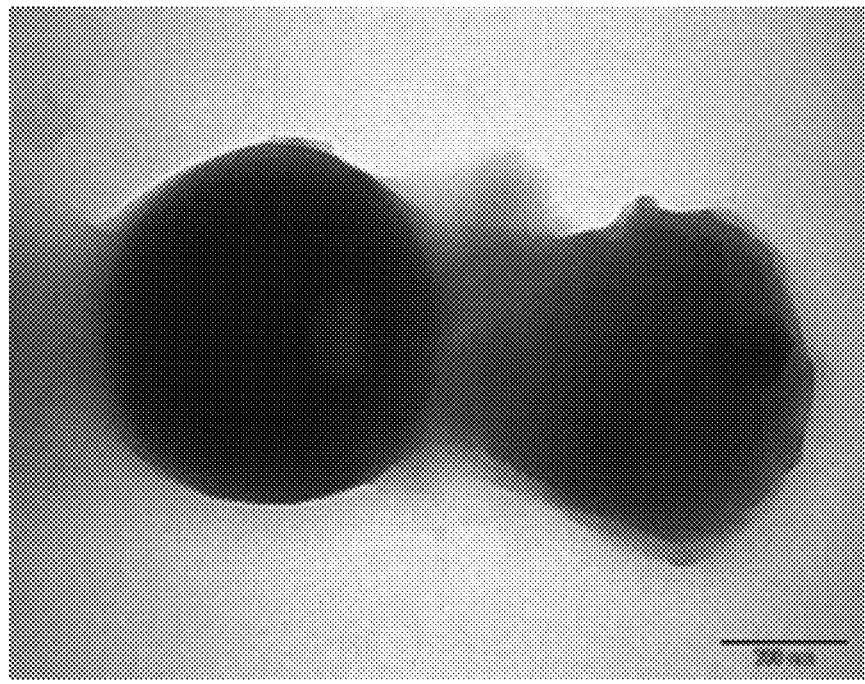
FIG. 5C is a TEM image of nanocomposite HSS-3GPS-Tri.
Figure 5D:
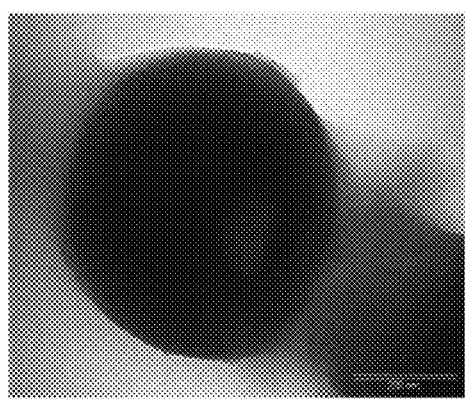
FIG. 5D shows a magnified view of the sample in FIG. 5C.
Figure 5E:
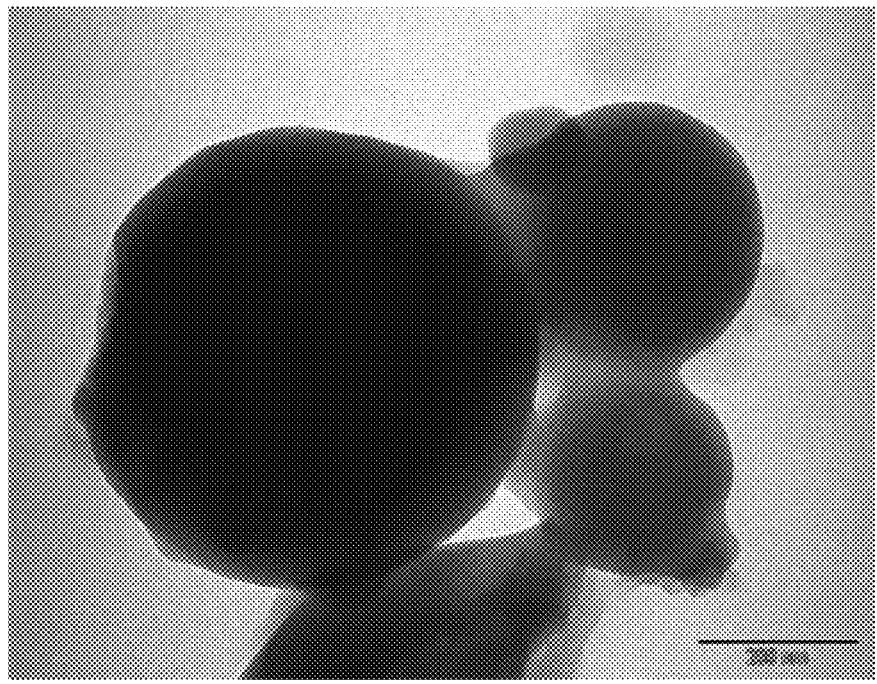
FIG. 5E is a TEM image of nanocomposite HSS-3GPS-Atri.
Figure 5F:
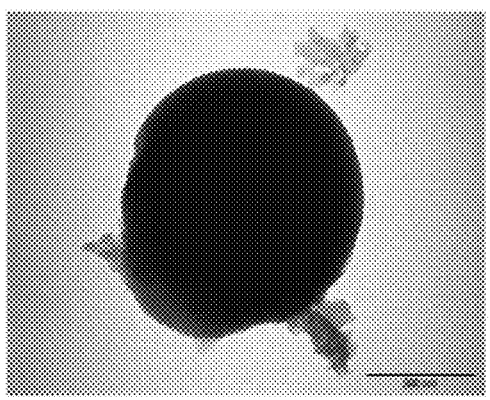
FIG. 5F shows a magnified view of the sample in FIG. 5E.
Figure 5G:
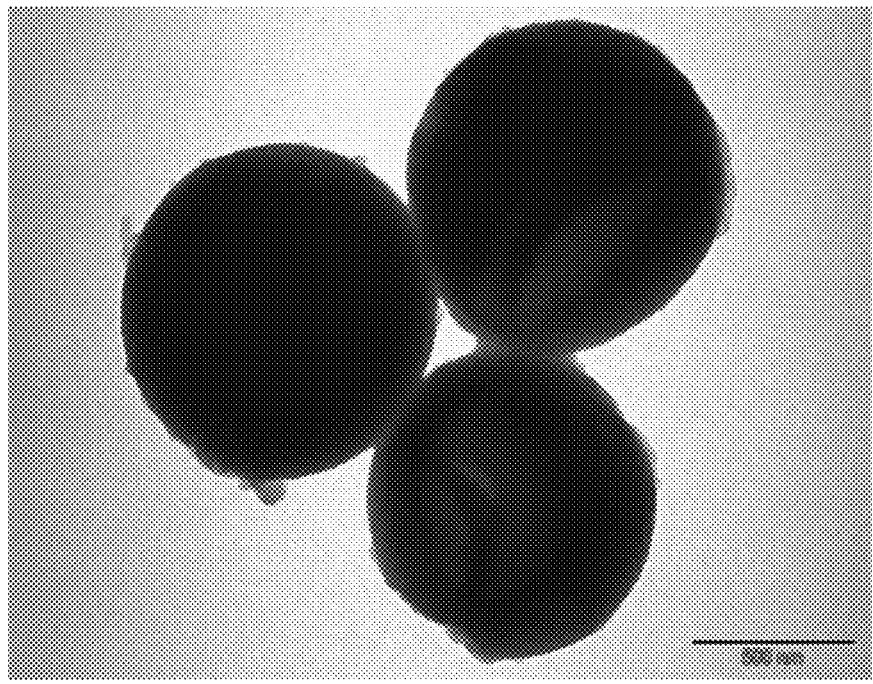
FIG. 5G is a TEM image of nanocomposite HSS-3GPS-Atet.
Figure 5H:
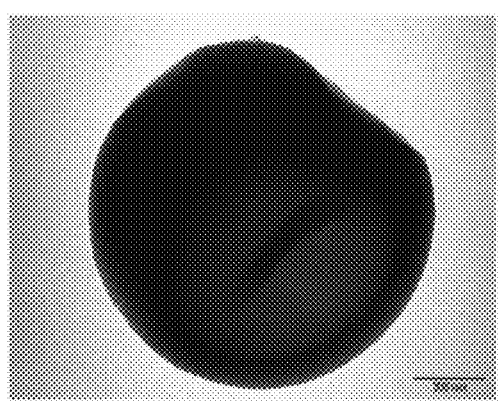
FIG. 5H shows a magnified view of the sample in FIG. 5G.

FIGS. 4A-D show FTIR spectra of pure HSS nanopartilces, and HSS-3GPS Azole nanocomposites. It was observed that several functional groups of absorption bands shared a similar frequency. In FIG. 4A, for HSS, absorption bands at 484 and 722 cm$^{-1}$ corresponded to Si—O out of plane deformation and Si—O bending, respectively [Li-Zhi Zhang, Qian-Wen Su, Performance manipulations of a composite membrane of low thermal conductivity for seawater desalination, Chemical Engineering Science, 192 (2018) 61-73, incorporated herein by reference in its entirety]. The intensity of these peaks declined significantly and shifted after azole addition with the frequencies to be around 425 and 748 cm$^{-1}$ (FIG. 2 (b-d)). For pure HSS, the strong peak at 926 cm$^{-1}$ was attributed to Si—OH stretching, whereas Si—O—Si stretching appeared at 1053 cm$^{-1}$ [Valmiki B Koli, Shielah Mavengere and Jung-Sik Kim, Photocatalytic properties of TiO$_2$—SiO$_2$-coated concrete on toluene gas, Materials Research Express, volume 5, 2018, incorporated herein by reference in its entirety]. The bands at 698, 1442, and 3100 cm$^{-1}$ indicated the asymmetrical stretching vibration of CH groups of aromatic phenyl [Gobi Nallathambi, Thangavelu Ramachandran, Venkatachalam Rajendran, Rajagoundar Palanivelu, Effect of Silica Nanoparticles and BTCA on Physical Properties of Cotton Fabrics, Materials Research. 2011; 14(4): 552-559, incorporated herein by reference in its entirety].

After functionalization with azole group, broad peaks at 3330, 3356, and 3319 cm$^{-1}$ were observed for HSS-3GPS-Tri, HSS-3GPS-Atri, and HSS-3GPS-Atet, respectively, which were attributed to —OH formed from the ring-opening reaction of the epoxy group. Interestingly, two new peaks appeared between 2920-2850 cm$^{-1}$ assigned to to CH$_2$ were seen for HSS-3GPS-Azole samples [UbongEduok, Rami Suleiman, MazenKhaled, Robert Akid, Enhancing water repellency and anticorrosion properties of a hybrid-silica coating on mild steel, Progress in Organic Coatings, 93(2016) 97-108, incorporated herein by reference in its entirety]. Other new peaks at 1643, 1633, and 1669 cm$^{-1}$ were observed for HSS-3GPS-Tri, HSS-3GPS-Atri, and HSS-3GPS-Atet, respectively, which were assigned to N=N bond. However, slight peak shifting and weakened intensity for CH peaks observed at 1418, 1428 and 1418 cm$^{-1}$ was evident after functionalization. For HSS-3GPS-Azole samples, (FIGS. 4B-D), distinctive bands with different intensities at around 1643 and 1561 cm$^{-1}$ corresponded to N=N and C=N stretching [Sevim Ünügür ÇelikÜmit Akbey, Ayhan Bozkurt, Robert Graf Hans W. Spiess, Proton-Conducting Properties of Acid-Doped Poly (glycidyl methacrylate)-1,2,4-Triazole Systems, Macromolecular Chemistry and Physics 209 (6), 593-603, 2008, incorporated herein by reference in its entirety].

Example 8

Morphological Studies

Figure 6A:
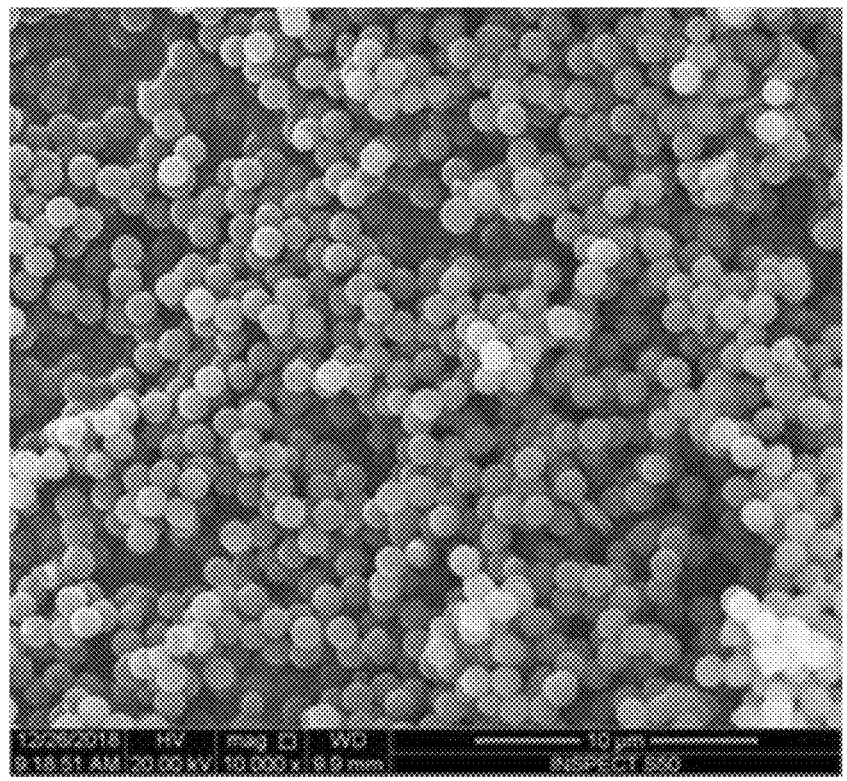
FIG. 6A is a SEM image of unmodified hollow silica spheres.
Figure 6B:
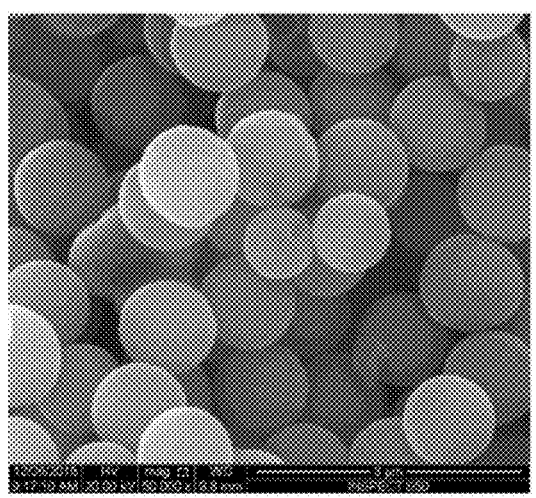
FIG. 6B shows a magnified view of the sample in FIG. 6A.
Figure 6C:
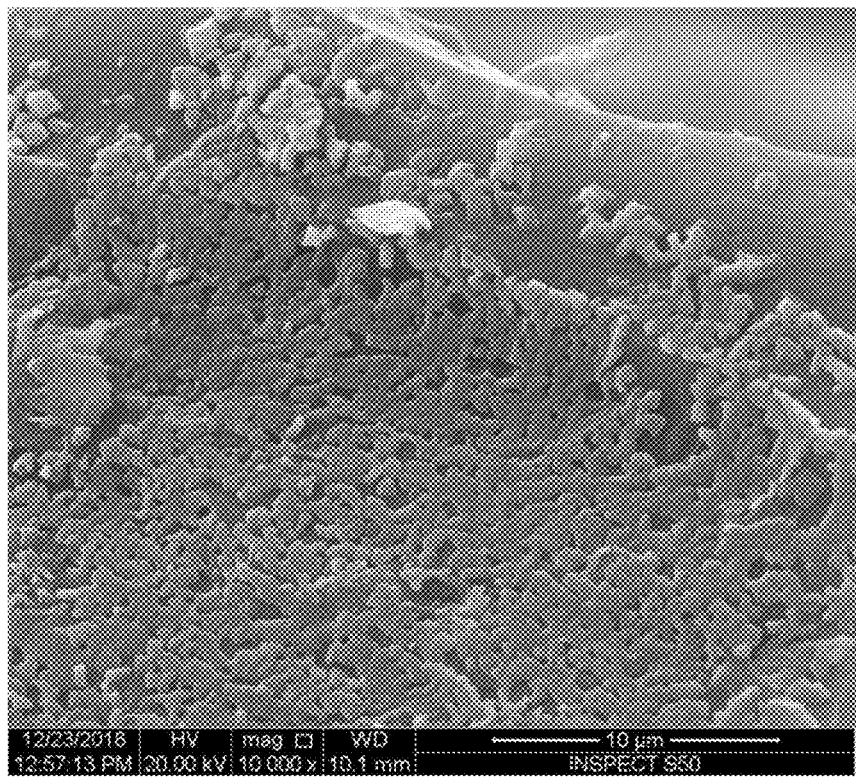
FIG. 6C is a SEM image of nanocomposite HSS-3GPS-Tri.
Figure 6D:
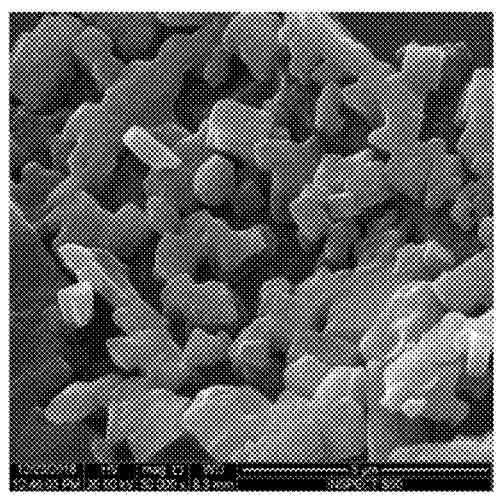
FIG. 6D shows a magnified view of the sample in FIG. 6C.
Figure 6E:
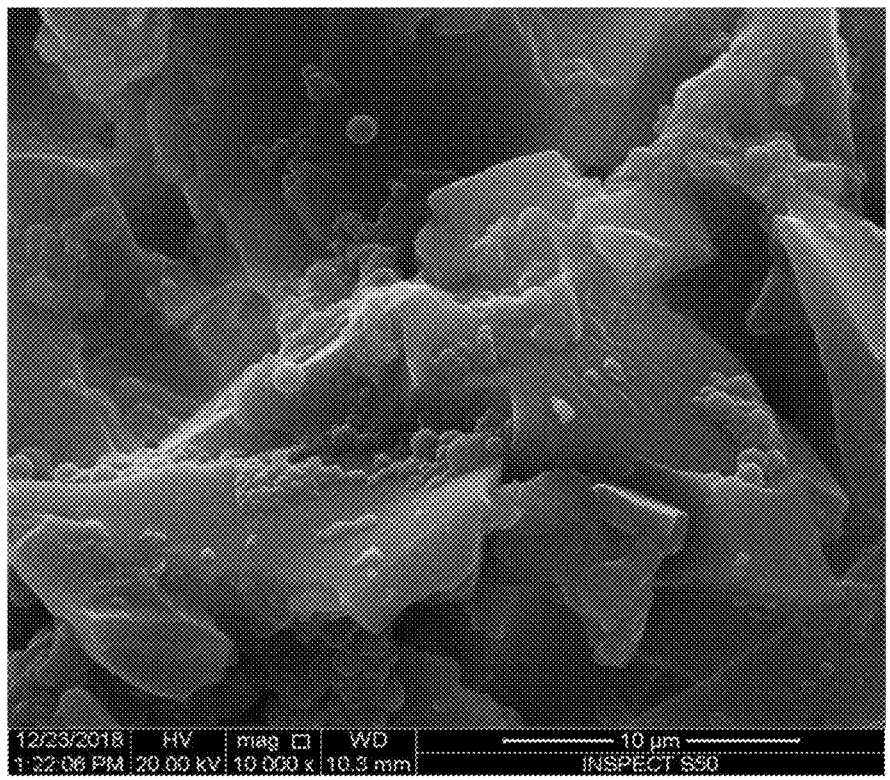
FIG. 6E is a SEM image of nanocomposite HSS-3GPS-Atri.
Figure 6F:
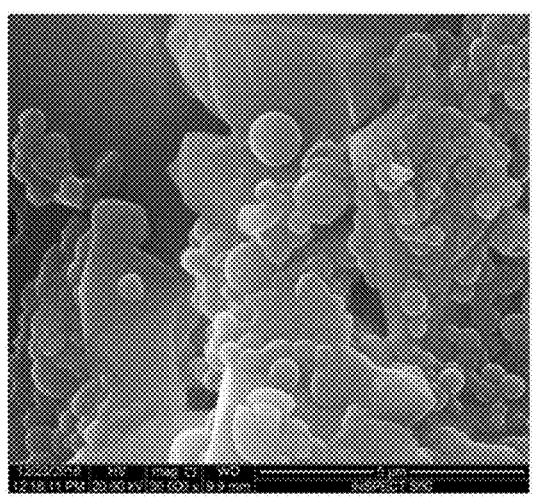
FIG. 6F shows a magnified view of the sample in FIG. 6E.
Figure 6G:
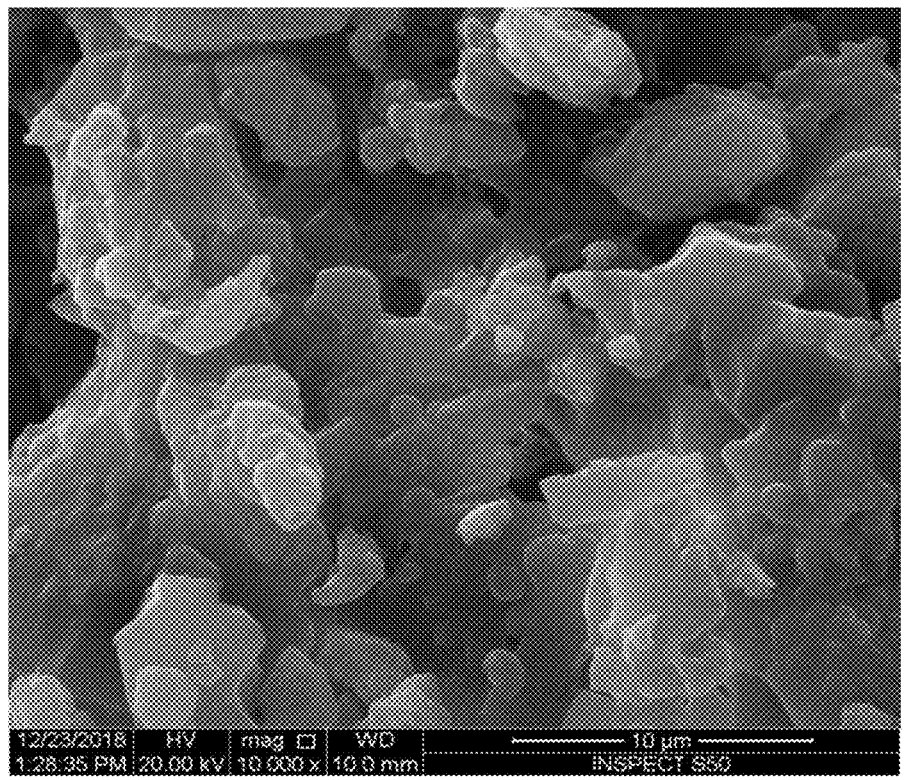
FIG. 6G is a SEM image of nanocomposite HSS-3GPS-Atet.
Figure 6H:
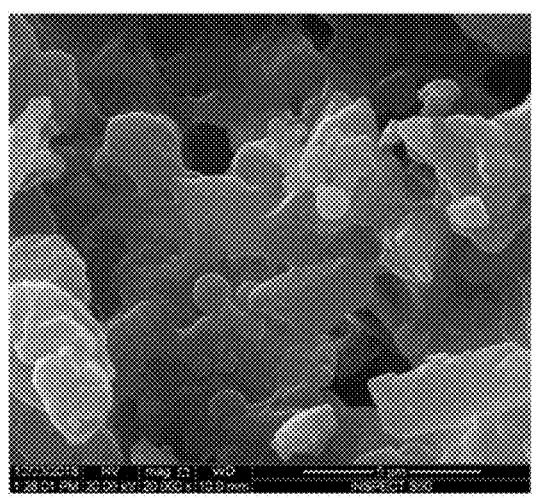
FIG. 6H shows a magnified view of the sample in FIG. 6G.

FIGS. 5A-H represent TEM images with low and high magnifications. Pure HSS nanoparticles (FIGS. 5A-B) exhibit a separated hollow spherical shape with a regular texture. These HSS nanoparticles had a uniform size distribution with a diameter of around 650 nm [H. J. Hah et al, Simple preparation of monodisperse hollow silica particles without using templates, Chemical Communications, 14 (14) (2003) 1712-1713, incorporated herein by reference in its entirety]. FIGS. 5C-H demonstrated the significant morphology change of HSS upon modification with the polymer and azole group. The azole functional group played a major role in covering the spherical hollow particles of HSS with a shell having a few nanometers thickness on the surface. In addition, the hollow spherical shape of the particles remained unchanged. The choice of polymer type has an enormous influence on the product structure, mainly by affecting the aggregation mechanism, which was responsible for the formation of HSS-3GPS-Azole nanoparticles. FIGS. 6A-B illustrate SEM characterization of pure HSS. It was observed that HSS was present in monodispersed spherical particles with a smooth and uniform surface, which was consistent with TEM results. However, the morpholgical feature of the samples changed noticeably after reacting with 3GPS-Azoles. For HSS-3GPS-Tri (FIGS. 6C-D), the GPS group acted to crosslink between HSSs and cover them completely, forming nanocubes. HSS-3GPS-Atri and HSS-3GPS-Atet (FIGS. 6 E-H) demonstrated different morphologies and irregular shapes, which confirmed the impact of polymers on both the bonds of the structures (as shown in the FT-IR results), and the shape and size of the nanomaterials.

Example 9

Thermogravimetric Measurement

Figure 7:
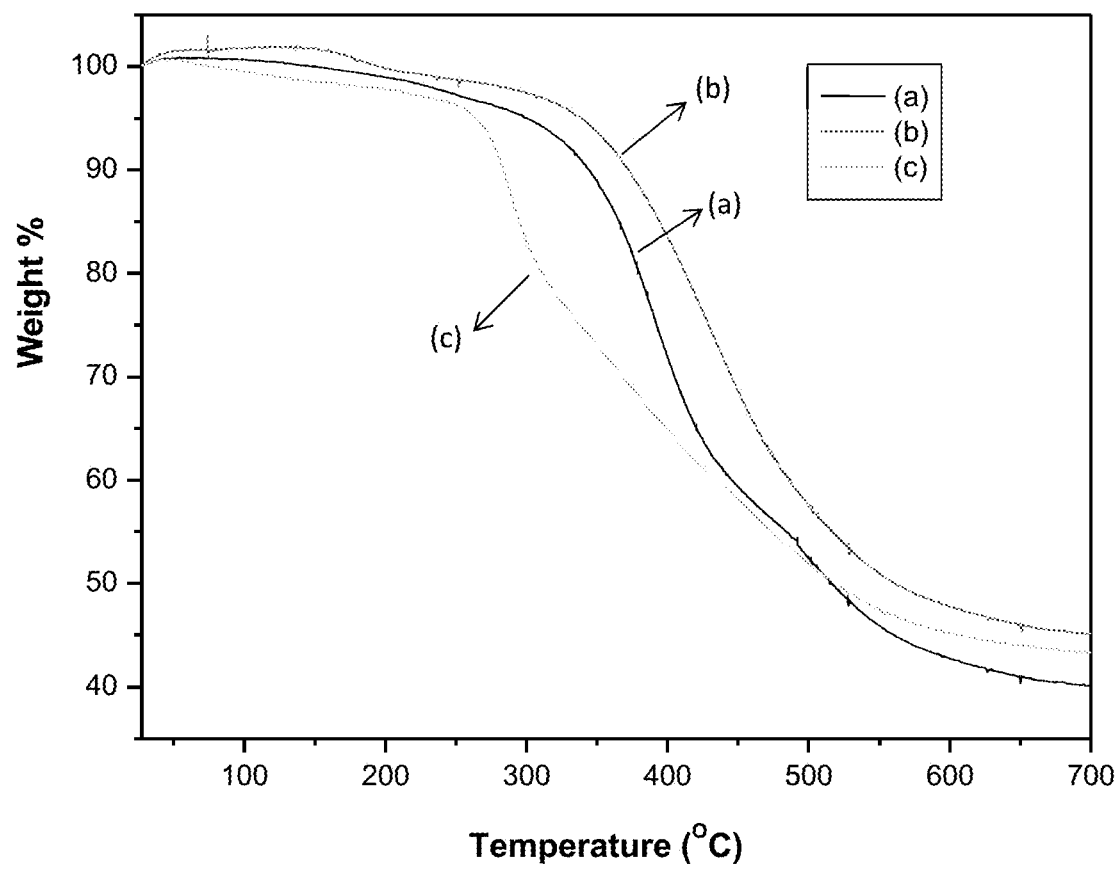
FIG. 7 is an overlay of thermogravimetric analysis (TGA) curves of nanocomposites HSS-3GPS-Tri, HSS-3GPS-Atri, and HSS-3GPS-Atet, respectively.

TGA diagrams (FIG. 7) describe a simple phase of weight loss and decomposition, and represent the quantity of polymer in a structure. A degradation temperature was in direct relationship with overall weight loss of nearly 60%, 55%, and 57% for HSS-3GPS-Tri, HSS-3GPS-Atri, and HSS-3GPS-Atet, respectively. The first step of the thermal decomposition of the samples was between 95° C. and 350° C., corresponding to the loss of azole functional oligomers which was about 5% of the total weight [Ayşe Aslan, Ali Murat Soydan and AyhanBozkurt, Synthesis and characterization of novel multifunctional polymer grafted hollow silica spheres, Journal of Materials Research, 2015 (30) 2408-2416, incorporated herein by reference in its entirety]. The substantial weight loss of 45% occured after 350° C., which might be due to deoxidative decomposition. The last stage (above 520° C.) could be attributed to the thermal decomposition of silanol group [ChenhuiJia, Yuchuan Li, Shujuan Zhang, TengFei and Siping Pang, Thermogravimetric analysis, kinetic study, and pyrolysis-GC/MS analysis of 1,1'-azobis-1,2,3-triazole and 4,4'-azobis-1,2,4-triazole, Chemistry Central Journal, 2018 (12) 1-13, incorporated herein by reference in its entirety].

Example 10

This work focuses on the preparation of a nanocomposite via post functionalization of pure Hollow Silica Spheres (HSS). Modifications of HSS was carried out using different types fo azole, including 1,2,4-Triazole (Tri), 3-Amino-1,2,4-triazole (Atri), and 5-Aminotetrazole monohydrate (Atet) with (3-Glycidyloxypropyl) trimethoxysilane (3GPS) to prepare HSS-3GPS-Tri, HSS-3GPS-Atri and HSS-3GPS-Atet, respectively.

The azole functional groups played a main role in covering the spherical particles of HSS with a shell of a few nanometers thickness on the surface. The morphology analysis by Transmission Electron Microscopy (TEM) and Scanning Electron Microscopy (SEM) depicted significantly how the azole group changed the morphology of HSS when the feature of the samples changed noticeably after azoles conjugation. TEM exhibits significantly how the polymer and azole group changed the morphology of HSS. Importantly, the functional azole played a main role to cover spherical hollow particles of HSS and showed shell with some nanometers thickness on the surface, while silica hollow spherical structures remained unchanged. Consequently, the choice of polymer type has an enormous influence on the product structure, mainly by affecting the aggregation mechanism, which stands responsible for the formation of HSS-3GPS-Azole nanoparticles. For HSS-3GPS-Tri the azole group worked to aggregate and coat HSS nanoparticles completely. Likewise, HSS-3GPS-Atri and HSS-3GPS-Atet demonstrate different morphologies and irregular shapes, which confirm that the effect of polymers is not only on the bonds of the structures as shown in the FTIR results, but also on the shape and size of nanomaterials.

The FTIR and XRD analysis showed the effect of the functionalized azole on the HSS structure through appearance new absorption peaks due to azoles group conjugation with HSS structures, which give HSS unique features and structure to be able to apply in different vital applications such as anti-cancer agents and tumor therapeutics.

The invention claimed is:

1. A nanocomposite, comprising a silanization reaction product of:
   a hollow silica sphere comprising a silica-containing shell surrounding a core; and
   an azole-functionalized silane linker,
   wherein:
   the silica-containing shell has a higher density of silica compared to the core;
   the hollow silica sphere has an average diameter of 300-900 nm;
   the azole-functionalized silane linker is a ring-opening reaction product of:
   a coupling agent of formula (I)

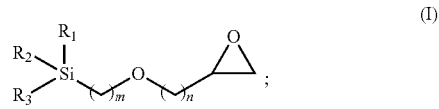

and
   an azole moiety selected from the group consisting of 1H-1,2,4-triazole, 3-amino-1,2,4-triazole, and 5-aminotetrazole,
   wherein:
   $R_1$ and $R_2$ are independently an optionally substituted $C_1$-$C_6$ alkoxy;
   $R_3$ is selected from the group consisting of an optionally substituted $C_1$-$C_6$ alkoxy, an optionally substituted alkyl, and an optionally substituted cycloalkyl;
   m is an integer in a range of 2-10; and
   n is an integer in a range of 1-6, and
   a weight ratio of the hollow silica sphere to the azole-functionalized silane linker is in a range of 2:1 to 50:1.

2. The nanocomposite of claim 1, wherein $R_1$ and $R_2$ are independently a methoxy, or an ethoxy.

3. The nanocomposite of claim 1, wherein $R_3$ is selected from the group consisting of a methoxy, an ethoxy, a methyl, and an ethyl.

4. The nanocomposite of claim 1, wherein m is 3.

5. The nanocomposite of claim 1, wherein n is 1.

6. The nanocomposite of claim 1, wherein the coupling agent of formula (I) is (3-glycidyloxypropyl)-trimethoxysilane, (3-glycidyloxypropyl)-triethoxysilane, or both.

7. The nanocomposite of claim 1, wherein a molar ratio of the coupling agent of formula (I) to the azole moiety is in a range of 1:2 to 2:1.

8. The nanocomposite of claim 1, wherein the hollow silica sphere comprises at least 85 wt % of silica relative to a total weight of the hollow silica sphere.

9. The nanocomposite of claim 1, wherein the silica-containing shell has a thickness in a range of 100-250 nm.

10. The nanocomposite of claim 1, wherein the core has a diameter in a range of 100-400 nm.

11. A method of preparing the nanocomposite of claim 1, the method comprising:
    mixing a hydrolyzable aryl silane and an acid in an aqueous solution to form a hydrolyzed silane solution;
    mixing the hydrolyzed silane solution with a hydroxide base to form a precipitate;
    drying the precipitate to form a hollow silica sphere;
    reacting a coupling agent of formula (I)

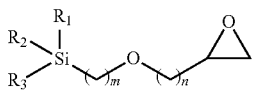
(I)

with an azole moiety selected from the group consisting of 1H-1,2,4-triazole, 3-amino-1,2,4-triazole, and 5-aminotetrazole to form an azole-functionalized silane linker;
mixing the hollow silica sphere and the azole-functionalized silane linker to form a mixture; and
heating the mixture thereby forming the nanocomposite, wherein:
$R_1$ and $R_2$ are independently an optionally substituted $C_1$-$C_6$ alkoxy;
$R_3$ is selected from the group consisting of an optionally substituted $C_1$-$C_6$ alkoxy, an optionally substituted alkyl, and an optionally substituted cycloalkyl;
m is an integer in a range of 2-10;
n is an integer in a range of 1-6; and
a weight ratio of the hollow silica sphere to the azole-functionalized silane linker is in a range of 2:1 to 50:1.

12. The method of claim 11, wherein the precipitate is dried at a temperature in a range of 50-150° C.

13. The method of claim 11, wherein the reacting occurs in an alcohol at a temperature in a range of 50-150° C.

14. The method of claim 11, wherein the mixture has a pH of 9-11.

15. The method of claim 11, wherein the heating is conducted at a temperature in a range of 40-100° C.

16. The method of claim 11, wherein the hydrolyzable aryl silane is trimethoxyphenylsilane.

17. The method of claim 11, wherein the acid is nitric acid, and wherein the hydroxide base is ammonium hydroxide.

18. The method of claim 11, wherein to the coupling agent of formula (I) is selected from 3-glycidyloxypropyl) trimethoxysilane or (3-glycidyloxypropyl)triethoxysilane.

* * * * *